United States Patent [19]
Tobia

[11] Patent Number: 5,735,267
[45] Date of Patent: Apr. 7, 1998

[54] ADAPTIVE CONTROL SYSTEM FOR A MEDICAL VENTILATOR

[75] Inventor: Ronald L. Tobia, Sun Prairie, Wis.

[73] Assignee: Ohmeda Inc., Liberty Corner, N.J.

[21] Appl. No.: 625,494

[22] Filed: Mar. 29, 1996

[51] Int. Cl.$^6$ ............................................. A61M 16/00
[52] U.S. Cl. ...................... 128/204.21; 128/204.23; 128/204.18
[58] Field of Search ............... 128/204.21, 204.28, 128/204.24, 204.18, 207.14, 207.15, 204.26, 204.23

[56] References Cited

U.S. PATENT DOCUMENTS

| | | | |
|---|---|---|---|
| 3,756,229 | 9/1973 | Ollives | 128/204.28 |
| 5,315,989 | 5/1994 | Tobia | 128/204.28 |
| 5,474,062 | 12/1995 | DeVries et al. | 128/204.27 |
| 5,546,935 | 8/1996 | Champeau | 128/207.14 |

Primary Examiner—Vincent Millin
Assistant Examiner—V. Srivastava
Attorney, Agent, or Firm—Roger M. Rathbun; Salvatore P. Pace

[57] ABSTRACT

A control system for a single-valve controlled medical ventilator adaptively invokes separate flow delivery or flow exhaust control functions in response to the sensed dynamic state of the ventilator without any dependence on measured patient parameters. The control system selects either the flow delivery control system or flow exhaust control system based on a determination of the mode in which the ventilator is operating. The determination is made using a sensed ventilator operational parameter, such as the ratio of manifold pressure to flow output, to select the appropriate control function. A hysteresis routine is provided to prevent "hair triggering" between the flow delivery and flow exhaust control systems.

22 Claims, 6 Drawing Sheets

FLOW DELIVERY CONTROL SYSTEM

ADAPTIVE CONTROL SYSTEM FOR A MEDICAL VENTILATOR

BACKGROUND OF THE INVENTION

The invention relates to medical ventilators and control systems therefor. Specifically, the invention relates to an apparatus for adaptive control of the flow and pressure of gases in a medical ventilator.

Medical ventilators provide respiratory support and anesthesia to patients undergoing medical treatment. The primary function of the ventilator is to maintain suitable pressure and flow of gases inspired and expired by the patient. Ventilators function in a variety of respiratory control modes, each depending on patient status and the judgement of the physician and anesthesiologist. Each modal application places different demands on the dynamic characteristics of the ventilator. For many applications, including intensive care unit (ICU) and anesthesia delivery applications, it is important for the ventilator to respond in a timely fashion to quick changes in target breathing patterns. In order to provide this degree of responsiveness for wide ranges of patient cases, ventilator systems must be adaptable to the variations in patient and ventilator dynamics that occur over the course of a single breath. Ventilator control systems thus require wide adaptability to provide adequate responsiveness throughout different modes of operation and during the changes in system dynamics that occur over the course of patient breathing.

In the past, mechanical implements have been utilized for the control of the flow and pressure of gases delivered to the patient. Ventilators incorporating such pneumatic hardware offered only limited modes of operation and frequently required many independently controlled valves and pneumatic circuits. Efforts to increase the adaptability of the ventilator to more modes of operation, or to increase the responsiveness of the ventilator control system, resulted in an increase in cost and complexity. There has thus developed a desire to implement relatively simple and inexpensive control systems that provide adequate responsiveness to quick changes in patient breathing patterns.

U.S. Pat. No. 5,315,989, issued to the present inventor discloses a medical ventilator with a single-valve control system for the flow and pressure of inspiratory and expiratory gases throughout the respiratory cycle. The single-valve control system is advantageous in reducing the complexity and cost of the ventilator. The valve is controlled via microprocessor for closed-loop minimization of the error between a sensed parameter, i.e., flow or pressure, and a predetermined reference signal provided by a waveform generator. The sensed parameter is thereby made to track the desired waveform selected in accord with patient breathing patterns and status.

Prior art systems of the type described in U.S. Pat. No. 5,315,989 work well when used in ventilation modalities consisting of bi-state valve control. For example, in performing Volume Ventilation, the flow valve of the prior art system is turned on to a specified level for the inspiratory period, then it is turned off to allow exhalation to occur. However, in modes of ventilation, such as Pressure and Positive End Expiration Pressure (PEEP) control, which require modulation of the flow valve, system responsiveness may be insufficient to achieve the response requirements of state of the art ICU and anesthesia ventilators. In these applications, required response times are typically less than 150 ms to achieve 63% full-scale output. Without this level of control responsiveness, the ventilator will be unable to generate sharp pressure waveforms and may even impose additional Work of Breathing (WOB) on patients respiring spontaneously.

One of the difficulties in designing a control system for ventilators of the type described in U.S. Pat. No. 5,315,989, lies in properly adjusting the control system to the vastly different dynamic characteristics of the ventilator as it repetitively passes from inspiratory to expiratory phases of a normal breath cycle. During the inspiratory phase of a patient breath, patient parameters, such as patient lung resistance and compliance, become a significant part of the patient-ventilator system and significantly affect ventilator response. In contrast, during the expiratory phase of a patient breath, patient parameters do not appreciably affect ventilator dynamics, which are then largely a function of the components of the ventilator itself.

Control systems tailored to produce acceptable responsiveness during the inspiratory phase of ventilator operation, which usually requires high gain, may become unstable when used to control ventilator dynamics during the expiratory phase of ventilator operation. On the other hand, control systems that are well-suited for expiratory phase of ventilator operation are too sluggish and lack sufficient response for adequate control during the inspirational phase of operation. Prior art attempts to solve these problems focused on independent mechanical functionality for control of the inspiratory and expiratory phases of operation. Such modifications add to the cost and complexity of the ventilator apparatus and do not easily lend themselves to application in the context of single-valve control systems.

Another drawback of prior art ventilator control systems like those described in U.S. Pat. No. 5,315,989, is that the these systems do not recognize or adapt to changes in the ventilator-patient system dynamics which may occur over the course of a single respiratory breath. For example, in pressure control modes, at the end of the inspiratory phase of a patient breath, the patient's lung will already have attained the target pressure of the ventilator. There will be no gas flow into the patient lung. Under these circumstances, the dynamic response of the ventilator will be equivalent to the dynamic response during the expiratory phase of operation, even though the patient is still in the inspiratory phase of the breath. Ventilator control systems which provide control based on timed inspiratory and expiratory periods, rather than the actual dynamic state of the ventilator, erroneously assume an inspiratory phase control model and provide inappropriate over-responsiveness under these conditions.

While prior art patient parameter-based control systems normally produce acceptable performance during the lung filling stages of inspiration, they may produce unstable performance during the latter stages of the inspiratory period where the lung is completely filled.

A closer inspection of the control problem as outlined reveals that an ideal control system for a ventilator such as that described in U.S. Pat. No. 5,315,989 must adaptively determine and adjust for variations in dynamic operation depending on the mode of operation of the ventilator, i.e., whether the ventilator is in a "flow delivery" or "flow exhaust" state of operation. As previously noted, these modes of operation do not necessarily coincide with the inspiratory and expiratory breath phases of the patient. This is particularly evident when the ventilator is used in an anesthesia application where a continuous amount of fresh gas flow is added to the breathing circuit throughout the inspiratory period. In this application the ventilator must transition to its "flow exhaust" state during the later stages of inspiration in order to prevent this fresh gas flow from raising the pressure of the full lung above its clinician-specified target level. Conversely, the ventilator may achieve a "flow delivery" dynamic state during the expiratory phase of a breath where fresh gas must be delivered to the breathing circuit in order to compensate for leakage in the ventilator-patient system or a spontaneous respiration.

Adaptive control schemes for medical ventilators have been disclosed in the prior art, but none to date are suited for implementation in ventilators utilizing single-valve control. Moreover, prior art systems do not control adaptation based on changes in the dynamic state of the ventilator. For example, U.S. Pat. No. 5,303,698 describes an adaptive control system for medical ventilator. The ventilator utilizes independent control of the inspiratory and expiratory branches of the ventilator to achieve high speed control of the pressure within a patient's mouth in accordance with a selected waveform. The system invokes separate inspiratory and expiratory control operations based on measured patient parameters. Hence, these prior art systems do not provide adaptive control that is based on the dynamic state of the ventilator. Moreover, while such systems may be adaptable to single-valve ventilators, they do not solve the control problem of managing the changing dynamic characteristics of "flow delivery" and "flow exhaust" states of operation.

There is thus a need for a medical ventilator control system which is adaptable to ventilators using single-valve control of inspiratory and expiratory flow and pressure and which provides adaptive control which is independent of measured patient parameters. Moreover, there is desired a ventilator control system which can sense the dynamic state of the single-valve ventilator and adapt its control parameters accordingly so as to provide ventilation response characteristics in all modes of operation which meet or exceed those of typical state-of-the-art anesthesia and ICU ventilators.

SUMMARY OF THE INVENTION

The present invention solves the problems of the prior art by providing an adaptive control system which selects a flow delivery control function or a flow exhaust control function depending on the dynamic state of the ventilator. Selection is based on a sensed operational parameter, such as the ratio of gas pressure to gas flow in the breathing circuit. Switching logic is provided with a hysteresis routing to prevent "hair triggering" between the flow delivery and flow exhaust control functions. Selection of the appropriate control system thus occurs as a function of the sensed dynamic state of the ventilator, without any dependence on measured patient parameters. The system is readily adaptable to a ventilator utilizing single-valve control.

DETAILED DESCRIPTION

Figure 1:
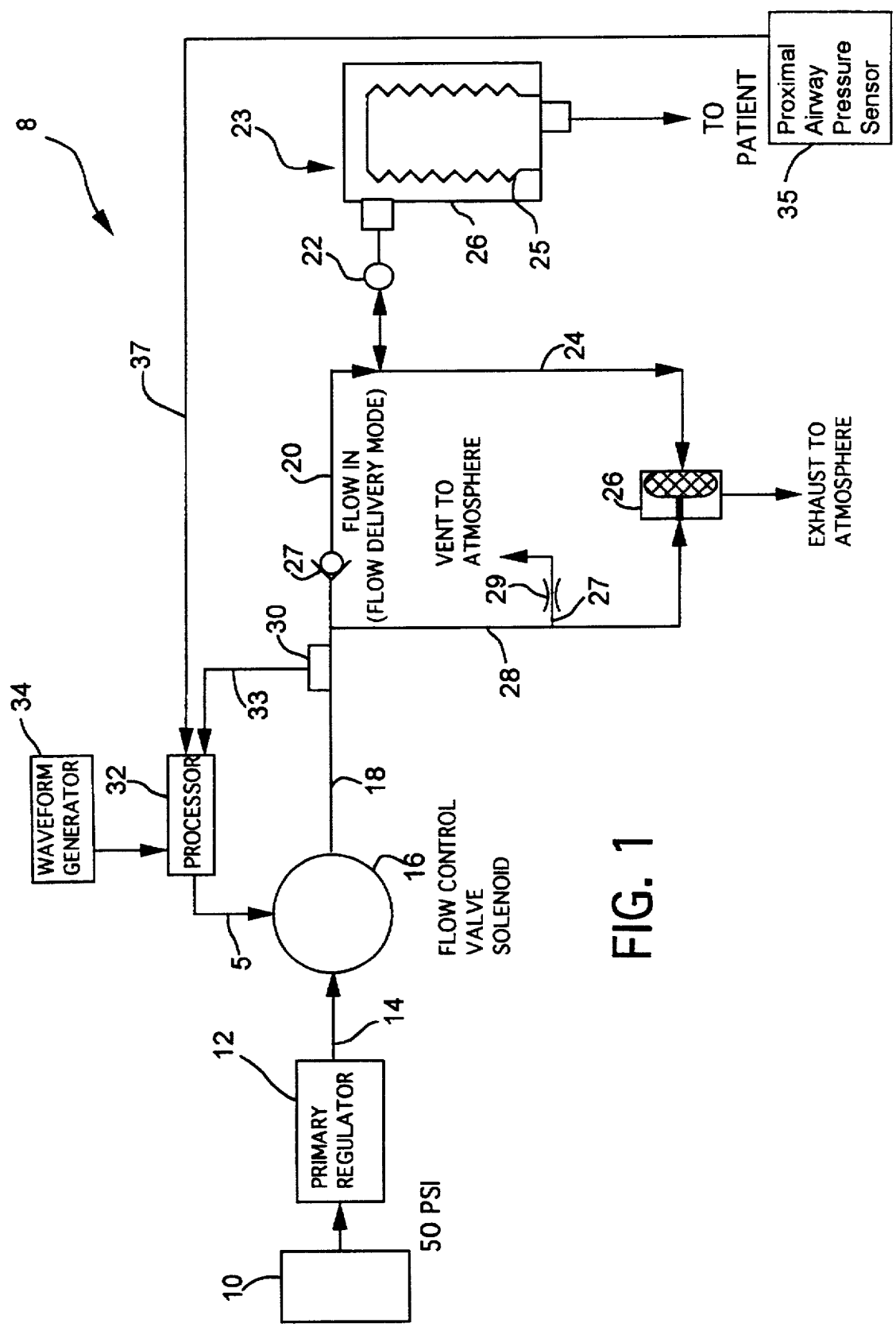
FIG. 1 is a schematic diagram illustrating a ventilator apparatus suitable for implementing a preferred embodiment of the present invention.

FIG. 1 schematically illustrates a medical ventilator apparatus suitable for implementing a preferred embodiment of the present invention. The mechanical aspects of the ventilator apparatus are similar to those disclosed in U.S. Pat. No. 5,315,989, the disclosure of which is incorporated herein by reference. It will be noted, however, that the mechanical embodiment of FIG. 1 differs from that described in FIG. 4 of U.S. Pat. No. 5,315,989 in that, for example, in accordance with the advantages of the present invention, the safety functionality previously provided by a safety valve to regulate the pressure provided to the expiratory valve is now simply achieved using on/off solenoid valve (not shown) disposed upstream of the control valve and controlled by the microprocessor. Other differences will be evident from the description which follows.

Ventilator 8 comprises a gas source 10, which typically provides pressurized gas at 50 psi, communicates through a primary regulator 12 with source conduit 14 which supplies flow control valve 4 with breathing gas at approximately 26 psi. Flow control valve 16 is preferably a proportional solenoid valve and controls the magnitude of gas flow into conduit 18. Conduit 20 communicates with conduit 18 and provides an inspiratory flow branch to ventilator connection 22. An expiratory flow branch is provided by conduit 24, which functions to convey gas from ventilator connection 22 to exhaust valve 26. Check valve 27 is located in conduit 20 to prevent flow from conduits 24 and 20 into conduit 18 during expiration of gas from patient connection 22.

Expiratory valve 26 controls the pressure and flow through conduit 24. Expiratory valve 26 is preferably a diaphragm or balloon type valve which is capable of controlling the pressure in conduit 24 according to a reference pressure. Reference control pressure is provided to expiratory valve 26 via pressure control conduit 28. A flow restrictor 29 is provided on vent conduit 27 to provide a control bleed from pressure control conduit 28. When pressure in expiratory conduit 24 exceeds the reference pressure in conduit 28, gas is exhausted from expiratory conduit 24 to the atmosphere. Thus, the pressure in expiratory conduit 24 is controlled by the reference pressure in pressure control conduit 28, which is in turn controlled by the flow control valve 16.

Ventilator connection 22 may be made to include a bellows assembly 23, as illustrated in FIG. 1, where conduit 20 communicates with bellows outer chamber 26 to actuate bellows 25. In this application, the patient's breathing tract is in communication with the interior of bellows 25 and thus isolated from the gas in ventilator 8. Alternatively, in an ICU application, bellows assembly 23 is omitted and ventilator connection 22 communicates directly with the breathing tract of the patient. Thus, in an ICU application, ventilator 8 provides breathing gas directly to the patient.

Pressure sensor 30 communicates with the interior of conduit 18 and provides a signal, indicative of the pressure in conduit 18, to processor 32 via signal line 33. The pressure in conduit 18 is hereinafter referred to as manifold pressure or $P_{man}$. Processor 32 includes a microprocessor connected via an electronic bus to read only memory (ROM) and random access memory (RAM) in a known digital computer configuration. Waveform generator 34 provides a desired pressure waveform to processor 32. Flow control valve solenoid 16 is controlled by processor 32 via control signal line 5 to track the desired pressure waveform as will be described below. Proximal airway pressure sensor 35, which is located at a point having a pressure that represents the pressure of the patient's airway, also provides signals to processor 32 via signal line 37.

Conduits 18, 20 and 24 define a ventilator circuit which communicates with the ventilator connection 22. During most of the inspiratory phase of a patient breath, the ventilator operates in a flow delivery mode whereby flow is delivered from gas source 10 through the flow control valve to conduits 18 and 20 and finally to the patient connection 22. During most of the expiratory phase of a patient breath, check valve 27 prevents flow from conduit 20 to conduit 18 and gas flows via conduit 24 to expiratory valve 26 where it is exhausted to the atmosphere. The ventilator thus operates in a flow exhaust mode.

It should be noted, however, that the operational modes of the ventilator do not necessarily coincide with the different phases of a patient breath. The ventilator may operate in a flow exhaust mode during the late stages of the inspiratory phase of a patient breath because the patient lungs may have already filled with breathing gas. The balance of gas delivered to conduit 20 will thus pass through conduit 24 and be exhausted through expiratory valve 26. Moreover, the ventilator may also operate in a flow delivery mode during the expiratory phase of a patient breath where flow input is necessary to compensate for leakage in the ventilator-patient system or the patient's spontaneous respiration effort.

Figure 2:
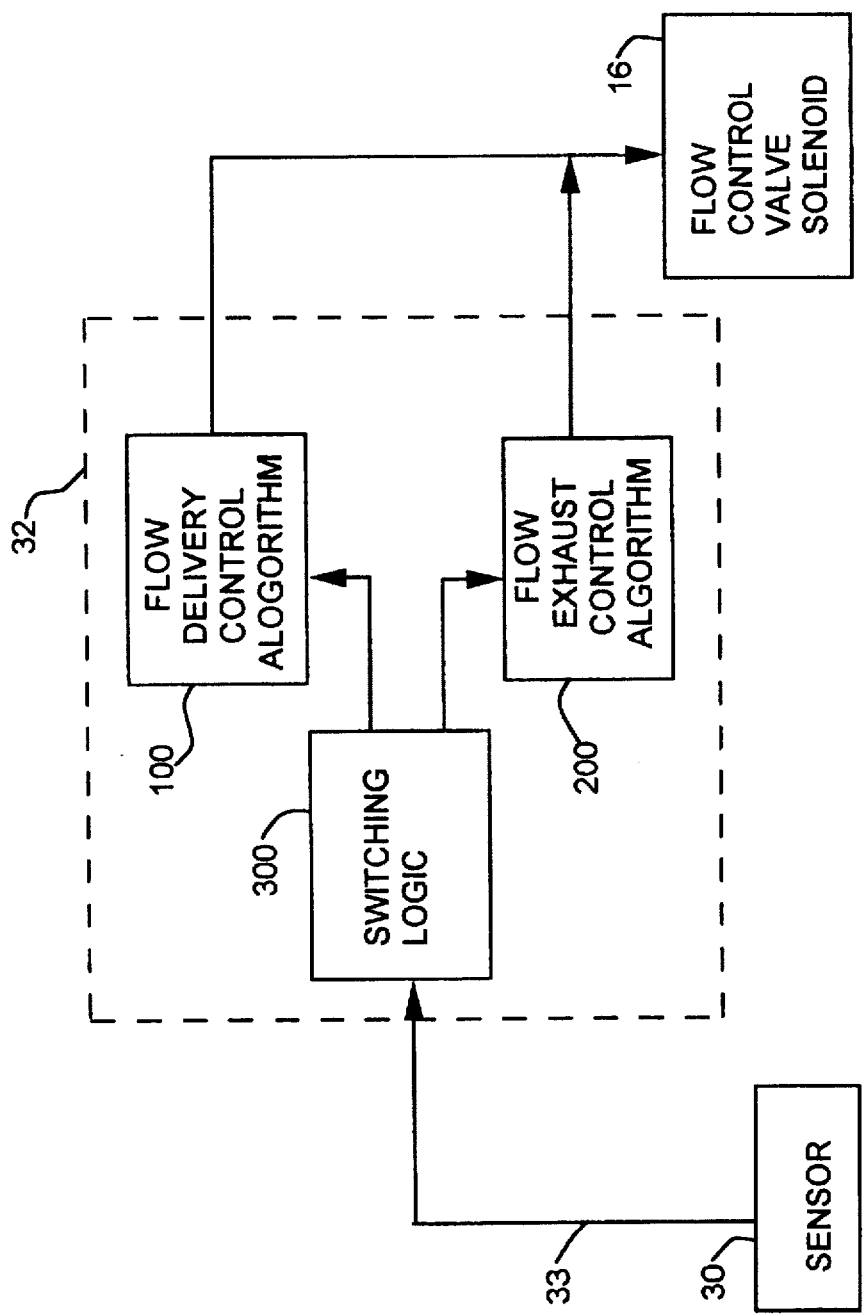
FIG. 2 is a block diagram illustrating a preferred embodiment of the present invention.

FIG. 2 represents the components of a control system according to a preferred embodiment of the present invention. Sensor 30 provides a signal on line 33 which represents the value of the pressure within conduit 18 (FIG. 1). The pressure value is input to the switching logic, represented by block 300, which provides a means for adaptively selecting either the flow delivery control algorithm 100 or the flow exhaust control algorithm 200. The selection is made based on an operational parameter which is indicative of the mode of operation of the ventilator. Preferably, the operational parameter is the ratio of the pressure to the flow of gas in conduit 18. The flow of gas in conduit 18 is provided to switching logic 300 by way of the command signal currently being issued to the flow control valve solenoid 16. As represented by the dotted line, switching logic 300, flow delivery control algorithm 100, and flow exhaust control algorithm 200 are implemented using software instructions to processor unit 32.

Figure 3:
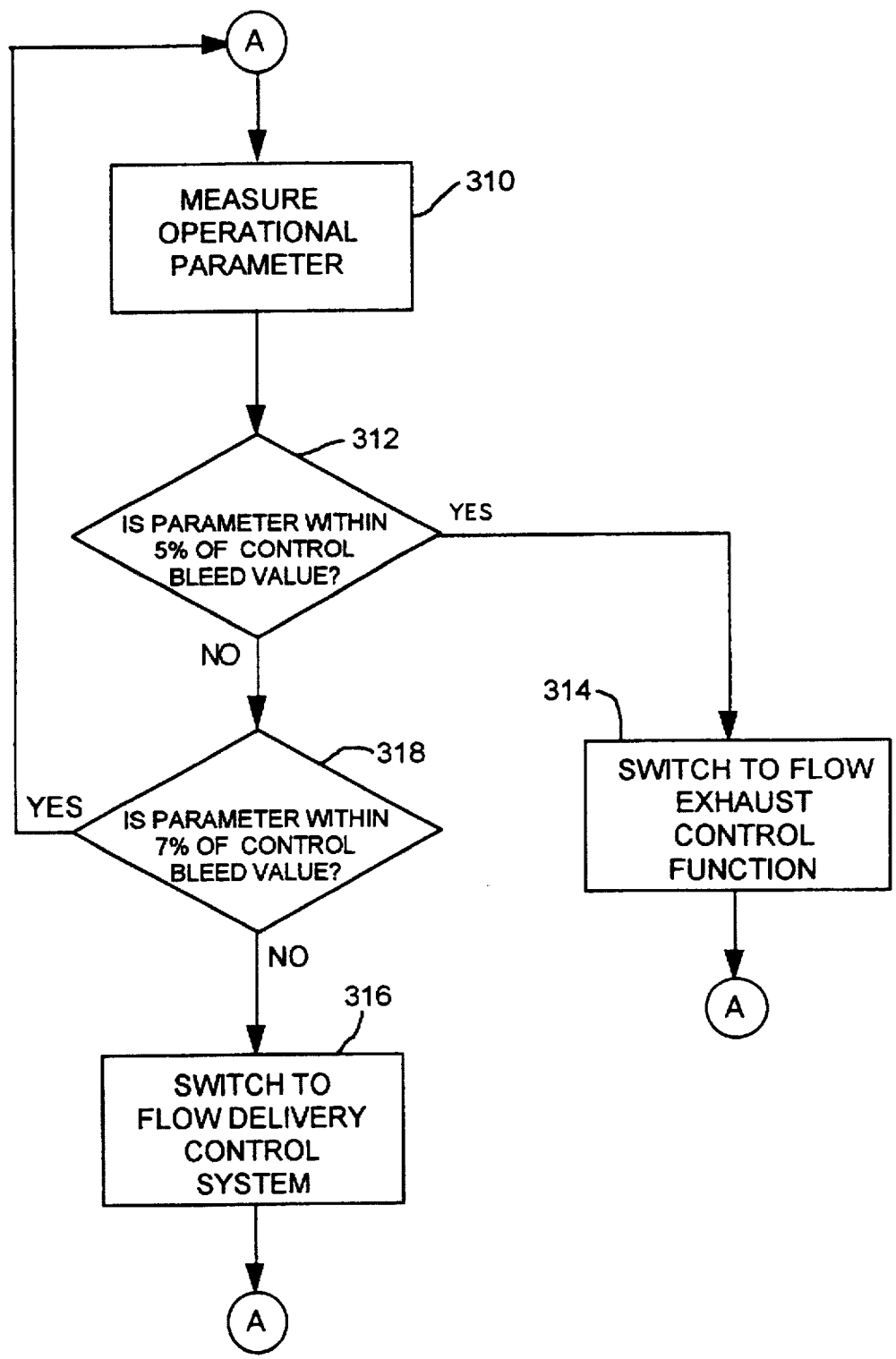
FIG. 3 is a flow chart depicting the switching logic of a preferred embodiment of the present invention.

Referring to FIG. 3, the adaptive selection of the appropriate control function by switching logic 300 incorporates a hysteresis routine to prevent hair triggering between the two control functions. At block 310, the operational parameter, i.e., the pressure/flow ratio, is determined using the signal from sensor 33 (FIG. 1) and the flow command signal being issued to the flow control valve solenoid. At 312, the logic determines whether the operational parameter is within a first tolerance, preferably less than +5%, of a value corresponding to the control bleed value of the parameter. The control bleed value is predetermined and corresponds to the operational parameter value, i.e. pressure/flow ratio that occurs when all of the flow output of the flow valve exits the ventilator through restrictor 29. If the operational parameter is within this tolerance of the control bleed values, the flow exhaust control function is invoked at block 314. The ventilator may already be operating in the flow exhaust mode, in which case the ventilator control function remains unchanged.

If the operational parameter falls outside of the 5% range of the control bleed value, the switching logic delays selection of the flow delivery control function. Decision block 316 causes the switching logic to loop back to the start of the routine, represented by terminal "A" until the operational parameter falls outside a second tolerance, preferably greater than +7% of the control bleed value, as represented by block 318. The two tolerances thus represent a "deadband" wherein the switching logic delays selection of the flow delivery control function until the operational parameter falls outside of the deadband. This prevents "hair triggering" or rapid cycling between inspiratory and flow exhaust control functions which may occur during low inspiratory flows or transitions in the dynamic state of the ventilator. Hair triggering may occur, for example, when the switching module triggers selection flow exhaust control system and immediately causes the operational parameters to fall out of tolerance. The control logic depicted in FIG. 3 operates in a continuous loop, as denoted by the connection terminals "A". Typically, the loop can be executed within 4 milliseconds by a digital computer, which provides many iterations during a single patient breath.

It is preferable to control the selection of the flow exhaust control mode using the +5% tolerance on the pressure/flow ratio discussed above. However, the selection of the flow delivery control mode is preferably based on the proximal air pressure sensed by sensor 35. It will be understood that other forms of hysteresis or "dead-bands" may be implemented in place of those described above. For example, time-based hysteresis may be provided where a switch back to the previous control mode is disabled for a given time such as 300 mS.

Figure 4:
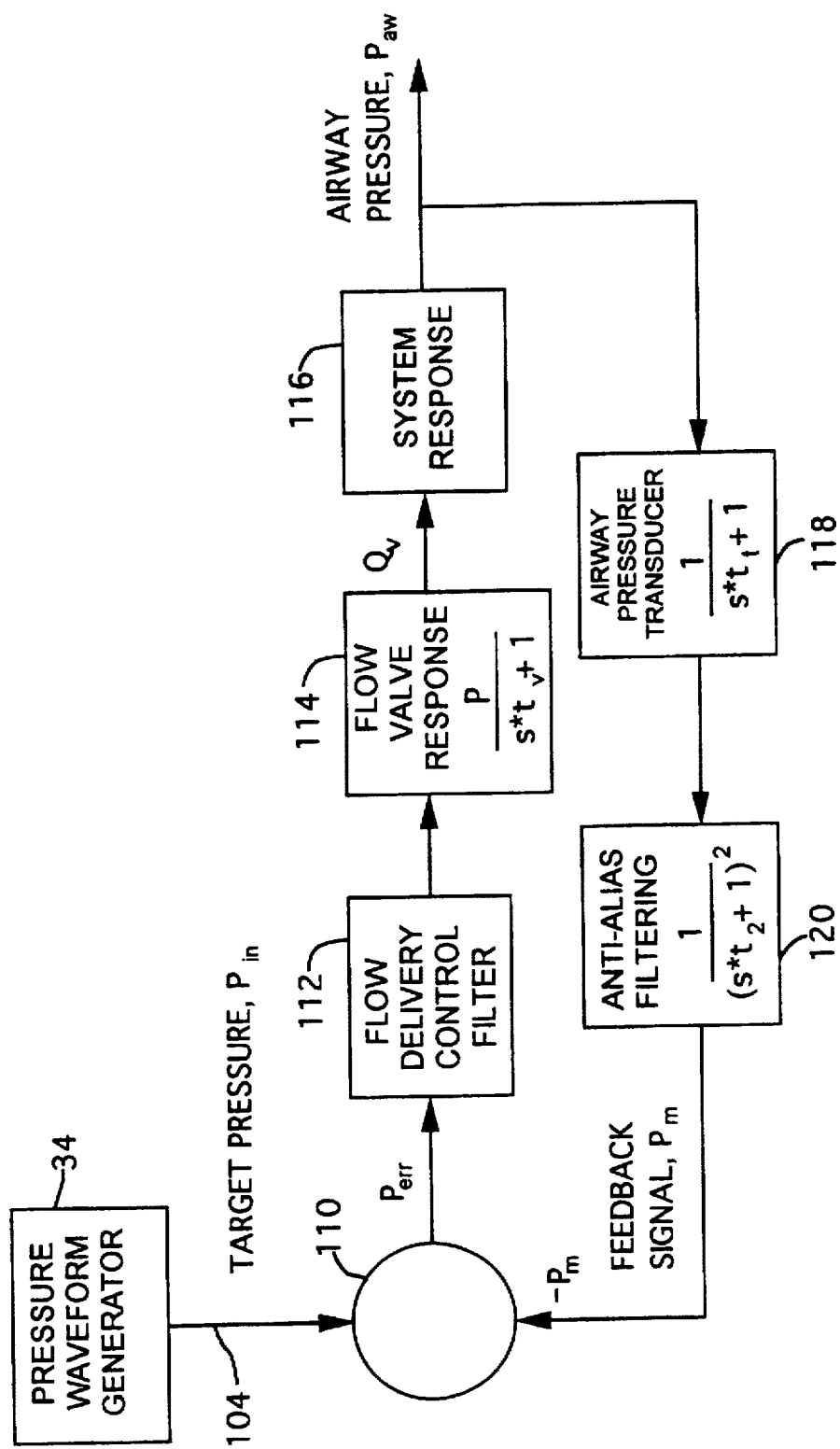
FIG. 4 is a block diagram illustrating a flow delivery control system according to a preferred embodiment of the present invention.
Figure 5:
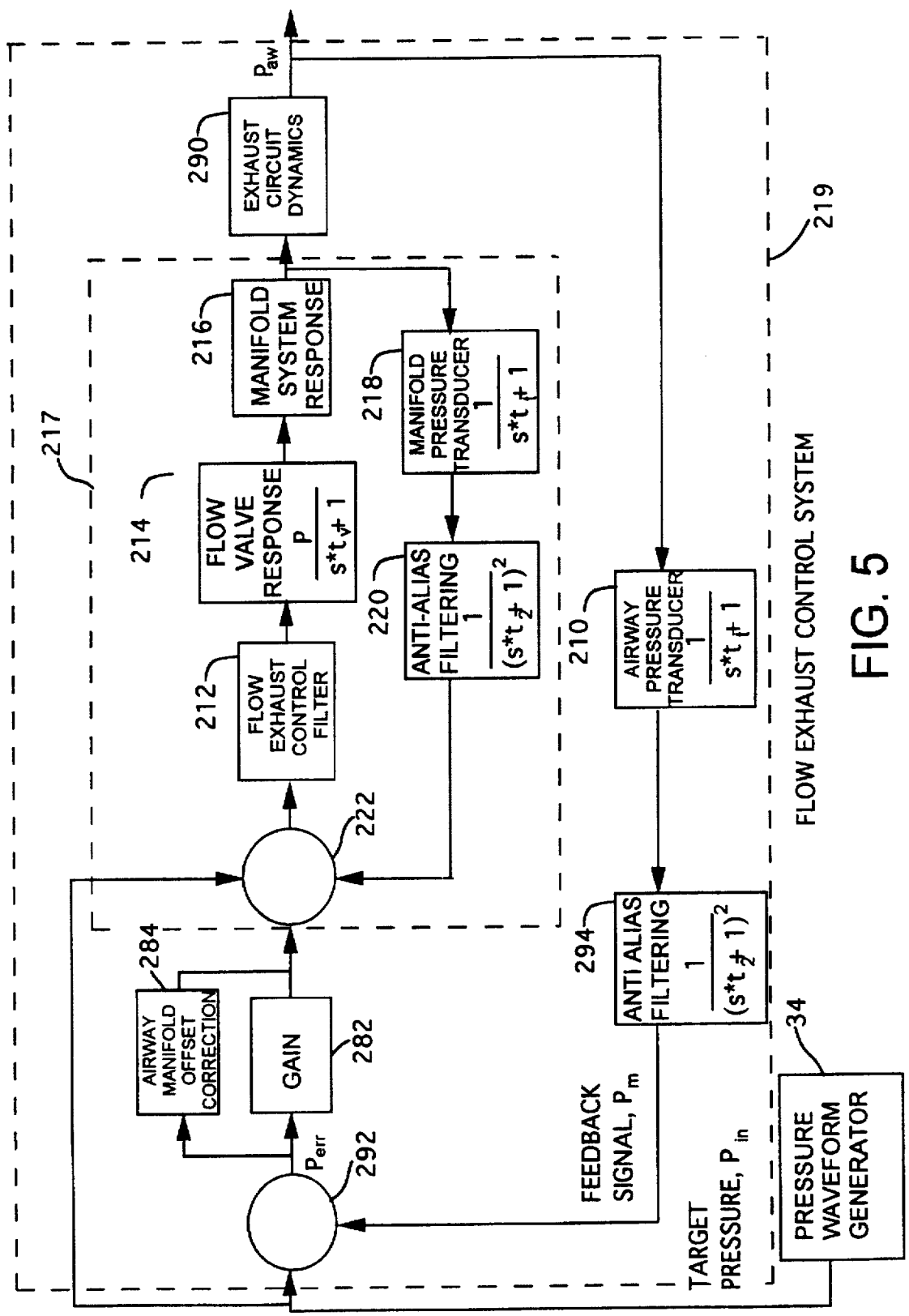
FIG. 5 is a block diagram of a flow exhaust control system according to a preferred embodiment of the present invention.

FIGS. 4 and 5 depict, in block diagram form, models of the flow delivery and flow exhaust control systems in conjunction with the response characteristics of the ventilator apparatus. Both control systems comprise negative feedback loops for minimizing the error between a target pressure signal, $P_{in}$ from pressure waveform generator 34 and a feedback signal corresponding to airway pressure $P_{aw}$. FIG. 4 represents a preferred embodiment of a flow delivery control system according to a preferred embodiment of the invention. Referring to FIG. 4, waveform generator 34 provides an input pressure signal, $P_{in}$ to summation block 110 where feedback signal $P_m$ is subtracted to provide a pressure error signal, $P_{err}$ to the flow delivery control filter 112. Flow delivery control filter 112 implements the s-domain flow delivery control function:

$$K * \frac{(T_1 * s + 1)}{(T_2 * s + 1)}$$

here K is the control gain, nominally set to value of 5, $T_1$ is a control lead constant and $T_2$ is a control lag constant.

Blocks 114 and 116 represent the response of the flow valve and ventilator system. Applicants have found that satisfactory control is achieved by using a generic model of the flow delivery system lumped parameter response 116 by the equation:

$$\frac{P_{aw}}{Q_v} = \frac{R_b * (R_p * C_p * s + 1)}{(R_b * C_c * R_p * C_p) * s^2 + (R_b * (C_c + C_p) + R_p * C_p) * s + 1}$$

where $R_b$ is the bleed resistance through resistor 29; $R_p$ is the patient airway resistance; $C_c$ is the overall ventilator circuit compliance including that of bellows 25; $C_p$ is the patient lung compliance; $Q_v$ is the valve flow and $P_{aw}$ is the airway pressure.

Control filter 112 generates a valve command signal based on the error signal $P_{err}$. A feedback signal is provided through airway pressure transducer 118 and an analog anti-alias filter 120, which are represented by the transfer functions shown in FIG. 4.

FIG. 5 represents a preferred embodiment of the flow exhaust control system according to the present invention. It is important to note that the dynamic operational state represented by FIG. 5 does not always coincide with the exhalation phase of patient breathing. Rather, the state may occur during the inspiratory phase of a patient breath. For example, during a patient breath, the patient lung will reach a state where it is completely filled with breathing gases. The flow of gases from the breathing circuit delivery system to the patient is zero. However, in an anesthesia application, fresh gas is still being supplied to the system and must be released to maintain the airway pressure. As recognized by applicant, use of the flow delivery control system designed for optimal ventilator response during the inspiratory phase, such as that represented in FIG. 4, during this zero-flow inspiratory period may be inappropriate due to the higher gain characteristics of the system response. That is, a very small change in control valve output, i.e. flow, causes a relatively large change in pressure at the patient airway.

It will be understood that FIGS. 4 and 5 depict control systems that are optimized for use in a bellows-equipped anesthesia application. Different control models will apply to ICU applications.

Flow exhaust control system 200 comprises an inner control loop 217, which operates on the manifold pressure signal, $P_{man}$ and an outer control loop 219 which operates on airway pressure $P_{aw}$. Inner control loop 217 comprises the flow exhaust control filter 212, flow valve response 214, manifold system response 216, manifold pressure transducer 218 and anti-alias filtering 220. Summing block 222 combines the manifold pressure feedback signal and target pressure signals, $P_{m1}$ and $P_{in}$ together with the manifold pressure correction signal $P_{corr}$.

The outer control loop 219 is necessary to compensate for the exhalation valve dynamics. The outer control loop comprises inner control loop 217, anti-alias filter 294 and airway pressure transducer 210. The outer control loop 219 includes a proportional control stage, comprising a proportional gain 282 and an airway/manifold offset correction 284, which is adjusted in an integral fashion over several breaths. The outer control loop feeds a correction for manifold pressure to the inner loop's control target pressure based on airway pressure information. Exhalation valve/breathing circuit RC response, represented by block 290, is also included in the outer control loop of the system model. Summing block 292 is provided with a feedback signal resulting from the transformation of airway pressure through the airway pressure transducer 210 and anti-alias filter 294.

Flow exhaust control filter 212 is represented by the equation:

$$K * \frac{(T_1 * s + 1)}{s}$$

where K is the gain, nominally (0.033) and $T_1$ is control lead (0.120).

Manifold system response 216 is represented by the equation:

$$\frac{P_m}{Q_v} = \frac{R_b}{(R_b * C_m * s + 1)}$$

where $C_m$ is pneumatic manifold compliance (upstream of drive gas check valve); $R_b$ is the bleed resistance; $Q_v$ is the valve flow and $P_m$ is the airway pressure.

The exhaust circuit dynamics during release of gas from ventilator in the flow exhaust mode is represented by block 290 and the equation:

$$\frac{P_{aw}}{P_m} = \frac{1}{(\tau * s + 1)}$$

Where $\tau$ is a function of the ventilator circuit compliance, tidal volume, patient parameters and exhalation valve resistance and is empirically determined.

Figure 6:
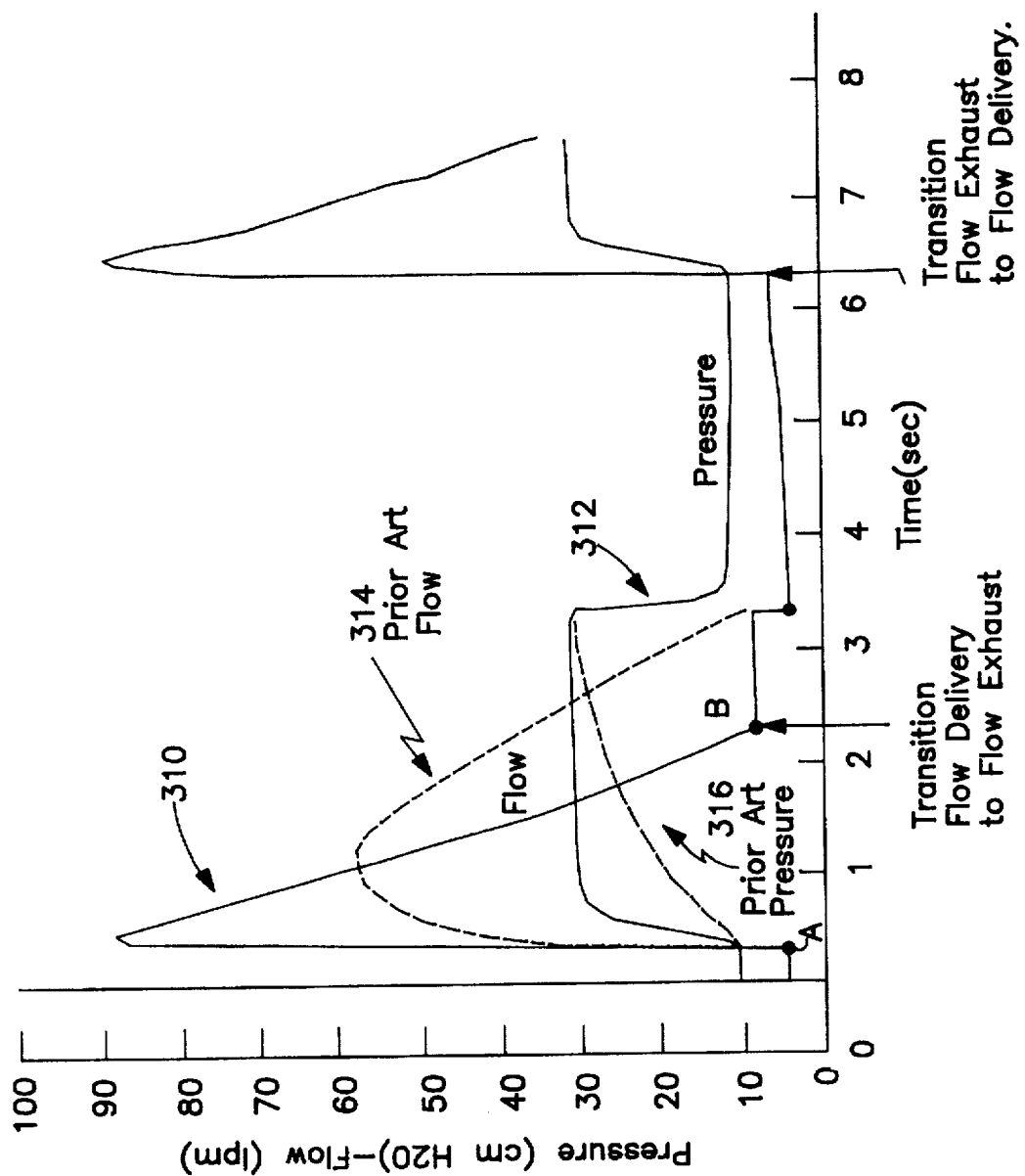
FIG. 6 illustrates flow and pressure response curves achieved according to the present invention and those of the prior art.

FIG. 6 represents the flow and pressure response achieved by a preferred embodiment of the invention. It will be understood that pressure is maintained at the desired level in a continuous fashion, despite the variations in flow that occur over the course of a patient breath. The solid line 310 represents flow response and the solid line 312 represent the pressure response achieved with a preferred embodiment of the present invention.

Point A represents a transition in the ventilator control dynamics from the flow exhaust mode to the flow delivery mode. In this illustration, the transition coincides with the onset of patient inspiration, represented by the rapid increase in flow. Flow rapidly increases and then decreases as the lungs become filled. Point B represents the point at which the patient lung is filled. Here, the ventilator control transitions from the flow delivery mode to the flow exhaust mode. The constant flow subsequent to point B is the control bleed flow, which operates to maintain the lung in a filled condition. The control bleed flow remains nearly constant until patient expiration begins at point C.

The flow response characteristic of prior art control systems is represented by the dotted line 314. It can be seen that the prior art flow response is much slower than that achieved by the present invention. This is due to the fact that prior art flow control systems required a relatively slow control function so as to maintain stability when performing in flow exhaust mode. The effect of this limitation is seen in prior art pressure response 316 which requires a significant time to rise to the target pressure during patient inspiration. In contrast, the pressure response 312 achieved by the present invention closely tracks the desired square waveform target pressure.

During the patient expiratory periods, the pressure and flow responses of the prior art and present invention are the same. This is because the control schemes of the present invention during the expiratory periods are similar to those of the prior art which provide adequate response characteristics during expiration. In accordance with the present invention, however, the transition to these schemes is based on the ventilator dynamic state instead of the respiratory periods of the patient.

Although particular embodiments of the present invention have been shown and described, many other embodiments incorporating the inventive teachings may be easily constructed by those skilled in the art. The foregoing description is intended to illustrate rather than limit the scope of the present invention which is defined by the claims that follow. Specifically, the disclosed control algorithms need not be utilized as other control functions may be used without departing from the scope of invention.

I claim:

1. A medical ventilator for providing gas to a ventilator connection in order to produce inhalation and exhalation ventilation cycles, said medical ventilator comprising:
   (a) a gas source;
   (b) a ventilator circuit communicating with the gas source for conveying gas to and away from the ventilator connection;

(c) valve means for controlling the flow of gas in said ventilator circuit;

(d) means for sensing an operational parameter which is indicative of a mode of operation of the ventilator, the ventilator operating in a flow delivery mode, or a flow exhaust mode;

(e) processor means, operatively connected to the means for sensing, for controlling the valve means according to a signal from said means for sensing which represents said operational parameter, the processor means including:

(i) a flow delivery control means for controlling the valve means when the ventilator is in the flow delivery mode;

(ii) a flow exhaust control means for controlling the valve means when the ventilator is in the flow exhaust mode;

(iii) means for adaptively selecting one of the flow delivery control means or the flow exhaust control means based on the signal from the said means for sensing;

whereby the ventilator is capable of adaptively switching between the flow delivery and flow exhaust control means within a single breath of a patient depending on the mode of operation of the ventilator and independent of whether said ventilator is in said inhalation cycle or said exhalation cycle.

2. The ventilator of claim 1, wherein the means for sensing comprises a pressure sensor located in the ventilator circuit and wherein the operational parameter is based upon the pressure of gas in the ventilator circuit.

3. The ventilator of claim 2, wherein the processor means includes means for determining the flow through the valve means based upon a command signal to the valve means from the processor means, and wherein the operational parameter is the ratio of the flow through the valve means to the pressure in the ventilator circuit.

4. The ventilator of claim 1, wherein the processor means comprises a digital computer.

5. The ventilator of claim 1, wherein the flow delivery control system comprises a closed-loop control system.

6. The ventilator of claim 1, wherein the flow exhaust control system comprises a closed-loop control system.

7. The ventilator of claim 1, wherein the means for adaptively selecting comprises means for delaying selection of the flow exhaust control system until the operational parameter falls outside a predetermined tolerance of a value corresponding to the flow exhaust mode of operation, whereby a dead-band is provided to prevent hair-triggering between the control systems.

8. The ventilator of claim 1, wherein the ventilator connection communicates directly with a patient's airway and wherein the ventilator functions as an intensive care unit ventilator.

9. The ventilator of claim 1, wherein the ventilator connection communicates with a bellows assembly for delivering breathing gas to a patient the ventilator operates as an anesthesia ventilator.

10. The ventilator of claim 1, wherein the means for adaptively selecting comprises means for delaying selection of the flow exhaust control system until a predetermined time has expired.

11. A medical ventilator for producing inhalation and exhalation ventilation cycles comprising:

(a) a gas source;

(b) a first inspiratory flow branch communicating with the gas source for conveying gas to a ventilator connection;

(c) a second inspiratory flow branch, in communication with the first inspiratory flow branch, such that the gas flows from the first inspiratory flow branch into the second inspiratory flow branch;

(d) an expiratory flow branch, in communication with the ventilator connection, such that an expiratory flow of gas travels from the ventilator connection into the expiratory flow branch;

(e) means for preventing flow from said expiratory flow branch to the first inspiratory flow branch;

(f) the ventilator operating in a flow delivery mode, or a flow exhaust mode;

(g) pressure control means for causing the pressure of gas comprising the expiratory flow to vary concomitantly with variations in the pressure of the gas within said first inspiratory conduit;

(h) control means for controlling the pressure control means and including:

(i) a flow delivery control system for controlling the pressure control means when the ventilator is in the flow delivery mode;

(ii) a flow exhaust control system for controlling the pressure control means when the ventilator is in the flow exhaust mode of operation;

(iii) means for adaptively selecting one of the flow delivery control system or the flow exhaust control system;

whereby the ventilator is capable of adaptively switching between the control systems within a single breath of a patient depending on the mode of operation of the ventilator and independent of whether said ventilator is in said inhalation cycle or said exhalation cycle.

12. The ventilator of claim 11, further comprising means for sensing pressure in the ventilator circuit.

13. The ventilator of claim 11, wherein the pressure control means comprises at least one valve and wherein the processor means includes means for determining the flow through the pressure control means based upon a command signal to the valve from the processor means.

14. The ventilator of claim 11, wherein the processor means comprises a digital computer.

15. The ventilator of claim 11, wherein the flow delivery control system comprises a closed-loop controller.

16. The ventilator of claim 11, wherein the flow exhaust control system comprises a closed-loop controller.

17. The ventilator of claim 11, wherein the means for adaptively selecting comprises means for delaying selection of the flow exhaust control system until the operational parameter falls outside a predetermined tolerance of a value corresponding to the flow exhaust mode of operation, whereby a dead-band is provided to prevent hair-triggering between the control systems.

18. The ventilator of claim 11, wherein the means for adaptively selecting comprises means for delaying selection of the flow exhaust control system until a predetermined time has expired.

19. The ventilator of claim 11, wherein the ventilator connection communicates directly with a patient's airway and wherein the ventilator functions as an intensive care unit ventilator.

20. The ventilator of claim 11, wherein the ventilator connection communicates with a bellows assembly for delivering breathing gas to a patient and the ventilator operates as an anesthesia ventilator.

21. A medical ventilator for providing gas to a ventilator connection in order to produce inhalation and exhalation ventilation cycles comprising: (a) a gas source;

(b) a ventilator circuit communicating with the gas source for conveying gas to and away from the ventilator connection;

(c) valve means for controlling the flow of gas in the ventilator circuit; and (d) control means for controlling the valve means comprising:
  (i) means for sensing an operational parameter in the ventilator circuit indicative of the dynamic state of the ventilator;
  (ii) a first control system for controlling the valve means when the sensed operational parameter is below a predetermined value;
  (iii) a second control system for controlling the valve means when the sensed operational parameter is above the predetermined value;
  (iv) means for adaptively selecting one of the first control system or the second control system depending on the sensed operation parameter;

whereby the ventilator is capable of adaptively switching between the control systems within a single patient breath depending upon the dynamic state of the ventilator independent of patient parameters and independent of whether said ventilator is in said inhalation cycle.

22. A medical ventilator for providing gas to a ventilator connection in order to produce inhalation and exhalation ventilation cycles, the ventilator being capable of operating in a first dynamic state or a second dynamic state, the ventilator comprising:

a gas source;

(b) a ventilator circuit communicating with the gas source for conveying gas to and away from the ventilator connection;

(c) valve means for controlling the flow of gas in said ventilator circuit;

(d) means for sensing an operational parameter which is indicative of the dynamic state of the ventilator;

(e) processor means, operatively connected to the means for sensing, for controlling the valve means according to a signal from said means for sensing which represents the operational parameter, the processor means including:
  (i) a first control system for controlling the valve means when the ventilator is in the first dynamic state;
  (ii) a second control system for controlling the valve means when the ventilator is in the second dynamic state;
  (iii) means for adaptively selecting one of the first control system or the second control system based on the signal from the said means for sensing;

whereby the ventilator is capable of adaptively switching between the first and second control systems within a single breath of a patient depending on the dynamic state of the ventilator and independent of whether said ventilator is in said inhalation cycle or said exhalation cycle.

* * * * *